United States Patent
Sansoucy et al.

(10) Patent No.: US 11,638,589 B2
(45) Date of Patent: May 2, 2023

(54) ROTATABLE SURGICAL INSTRUMENT WITH BEARING

(71) Applicant: GYRUS ACMI, INC., Southborough, MA (US)

(72) Inventors: Michael Sansoucy, Wrentham, MA (US); James Harr, Southborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 274 days.

(21) Appl. No.: 17/026,526

(22) Filed: Sep. 21, 2020

(65) Prior Publication Data

US 2021/0100563 A1 Apr. 8, 2021

Related U.S. Application Data

(60) Provisional application No. 63/001,586, filed on Mar. 30, 2020, provisional application No. 62/910,542, filed on Oct. 4, 2019.

(51) Int. Cl.
*A61B 17/16* (2006.01)
*A61B 17/00* (2006.01)

(52) U.S. Cl.
CPC .............. *A61B 17/1615* (2013.01); *A61B 2017/00486* (2013.01); *A61B 2217/005* (2013.01); *A61B 2217/007* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 5,494,359 A * 2/1996 Del Rio ................. F16C 19/54
384/535
5,823,774 A 10/1998 Abbott et al.
(Continued)

FOREIGN PATENT DOCUMENTS

DE 102008045179 A1 3/2010
EP 2623049 A1 8/2013
(Continued)

OTHER PUBLICATIONS

"European Application Serial No. 20199887.9, Extended European Search Report dated Aug. 6, 2021", 11 pgs.
(Continued)

*Primary Examiner* — Eric S Gibson
(74) *Attorney, Agent, or Firm* — Schwegman Lundberg & Woessner, P.A.

(57) ABSTRACT

A rotatable surgical instrument and method includes an outer tubular member and an inner tubular member contained, at least in part, within the outer tubular member and configured to rotate relative to the outer tubular member, the inner tubular member and outer tubular member forming a gap therebetween. A distal tip is coupled to and configured to rotate with the inner tubular member. Bearings, each positioned in the gap and encircling the inner tubular member, are configured to maintain a separation between the outer tubular member and the inner tubular member. A spacer is positioned within the gap and between two of the bearings, wherein the spacer is configured to maintain a spacing between the bearings.

20 Claims, 5 Drawing Sheets

(58) Field of Classification Search
CPC ............ A61B 17/1622; A61B 17/1624; A61B 17/1626; A61B 17/1628; A61B 17/1631; A61B 17/1633; A61B 17/1657; A61B 17/1659

See application file for complete search history.

(56) References Cited

U.S. PATENT DOCUMENTS

| | | | |
|---|---|---|---|
| 6,209,886 B1* | 4/2001 | Estes | B23B 51/126 |
| | | | 279/143 |
| 8,221,424 B2 | 7/2012 | Cha | |
| 9,877,765 B2* | 1/2018 | Barth | A61B 17/8875 |
| 10,631,876 B2* | 4/2020 | Machill | F16C 33/40 |
| 10,772,668 B2* | 9/2020 | Barth | A61B 17/8866 |
| 11,207,081 B2* | 12/2021 | Voor | A61B 17/1717 |
| 2003/0023256 A1* | 1/2003 | Estes | A61B 17/1633 |
| | | | 606/167 |
| 2003/0219184 A1* | 11/2003 | Rio | A61B 17/1624 |
| | | | 384/523 |
| 2010/0063524 A1* | 3/2010 | McCombs | A61B 17/1628 |
| | | | 606/167 |
| 2013/0023900 A1* | 1/2013 | Nishio | A61B 17/1642 |
| | | | 606/130 |
| 2013/0184863 A1* | 7/2013 | Isobe | A61B 34/70 |
| | | | 74/471 XY |
| 2015/0238241 A1* | 8/2015 | Barth | A61B 17/1624 |
| | | | 606/86 R |
| 2015/0327905 A1* | 11/2015 | Barth | A61B 17/162 |
| | | | 606/104 |
| 2017/0007272 A1 | 1/2017 | Weitzman et al. | |
| 2017/0150975 A1 | 6/2017 | Bozung | |
| 2019/0015112 A1* | 1/2019 | Machill | F16C 33/40 |
| 2019/0239899 A1* | 8/2019 | Voor | A61B 17/1659 |
| 2021/0100563 A1* | 4/2021 | Sansoucy | A61B 17/1615 |
| 2022/0117612 A1* | 4/2022 | Schwamb | A61B 17/1615 |

FOREIGN PATENT DOCUMENTS

| | | | | |
|---|---|---|---|---|
| EP | 3799808 A2 * | 4/2021 | ......... | A61B 17/1615 |
| EP | 3988039 A1 * | 4/2022 | ......... | A61B 17/1615 |
| JP | 2021065697 A * | 4/2021 | ......... | A61B 17/1615 |
| JP | 2021065697 A | 4/2021 | | |
| WO | WO-0160261 A2 | 8/2001 | | |
| WO | WO-2014123874 A1 | 8/2014 | | |
| WO | WO-2022063390 A1 * | 3/2022 | | |

OTHER PUBLICATIONS

"European Application Serial No. 20199887.9, Partial European Search Report dated Mar. 5, 2021", 12 pgs.

"U.S. Appl. No. 17/026,526 Non Final Office Action dated Aug. 22, 2022", 8 pgs.

"European Application Serial No. 20199887.9,Response Filed Mar. 1, 2022 Extended European Search Report dated Aug. 6, 2021", 7 pgs.

* cited by examiner

ROTATABLE SURGICAL INSTRUMENT WITH BEARING

CROSS-REFERENCE TO RELATED APPLICATIONS

This application claims the benefit of priority to U.S. Provisional Patent Application Ser. No. 62/910,542 filed on Oct. 4, 2019 titled "ROTATIONAL COUPLER FOR A BURR" and U.S. Provisional Application Ser. No. 63/001,586 filed on Mar. 30, 2020 titled "ROTATABLE SURGICAL INSTRUMENT WITH BEARING"; the contents of which are incorporated herein in their entireties.

TECHNICAL FIELD

The subject matter disclosed herein generally relates to a flexible rotatable surgical instrument with bearings to facilitate rotation and inhibit lateral movement of the distal tip.

BACKGROUND

Rotatable surgical instruments have been utilized to perform surgical operations such as drilling, cutting, and the like. Such surgical instruments have included an elongate tubular member with a burr fixed to the end. The burr is induced to rotate at high speed to cut through material, up to and including bone and other hard materials.

BRIEF DESCRIPTION OF THE DRAWINGS

Some embodiments are illustrated by way of example and not limitation in the figures of the accompanying drawings.

DETAILED DESCRIPTION

Example methods and systems are directed to a flexible rotatable surgical instrument with a bearings to facilitate rotation and inhibit lateral movement of the distal tip. Unless explicitly stated otherwise, components and functions are optional and may be combined or subdivided, and operations may vary in sequence or be combined or subdivided. In the following description, for purposes of explanation, numerous specific details are set forth to provide a thorough understanding of example embodiments. It will be evident to one skilled in the art, however, that the present subject matter may be practiced without these specific details.

Because such surgical instrument may rotate at very high speeds, an outer tubular member or sheathe may be utilized to isolate certain rotatable portions from external interference, thereby protecting the surgical instrument as well as users of the rotatable instrument. However, the outer tubular member may interfere with the inner tubular member to which the burr or other distal tip is attached. As such, a bearing may be utilized to maintain separation between the inner tubular member and distal tip and the outer tubular member. However, the high rotational speeds may impart significant forces on the bearing and, if the bearing is not properly positioned along the inner and outer tubular members and with respect to the distal tip, may shift laterally with respect to the distal tip and inner tubular member. That may unbalance the rotatable instrument and/or cause undesired friction.

Moreover, the introduction of bearings and the like between the inner and outer tubular members may inhibit the capacity of the instrument to flex. The inclusion of elements between the tubular members may introduce additional friction when the instrument flexes, while flexing that does occur may cause the bearings to shift in annular relation to one another and to the distal tip, which may induce friction between the inner and outer tubular members.

A rotatable surgical instrument has been developed that incorporates multiple bearings positioned between the inner and outer tubular members. One or more spacers are positioned between adjacent bearings to maintain a minimum spacing or annular positioning between the bearings. To maintain bearings along the length of the inner tubular member, a distal bearing may be secured relative to the distal tip, e.g., with a retainer ring secured to one or more of the inner tubular member or distal tip.

Figure 1:
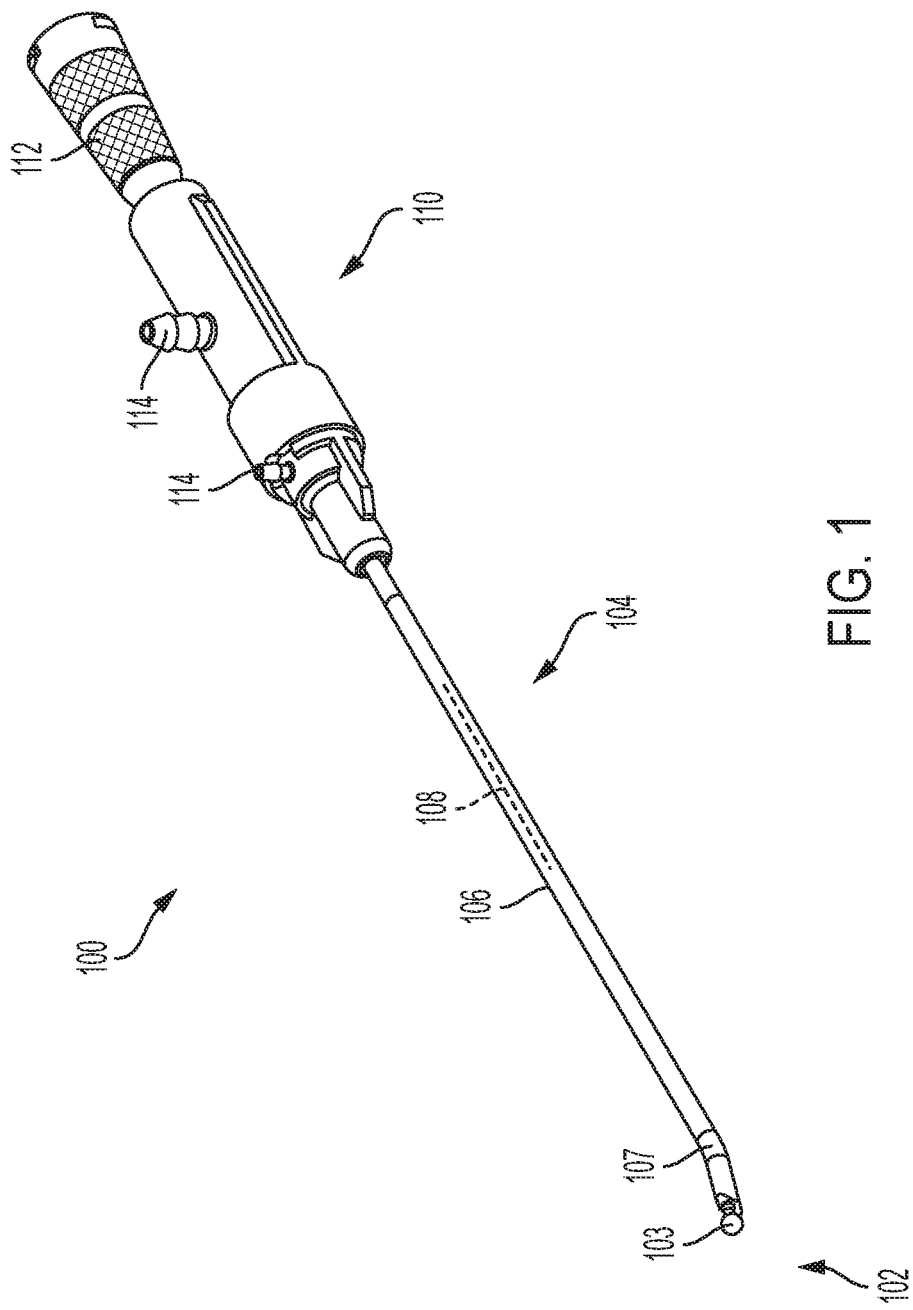
FIG. 1 is a cutaway image of a rotatable surgical instrument, in an example embodiment.

FIG. 1 is a cutaway image of a rotatable surgical instrument 100, in an example embodiment. The rotatable surgical instrument 100 includes a distal tip 102. In the illustrated example, the distal tip 102 includes a burr 103. In various alternative examples, the distal tip 102 is itself a burr or is or includes an alternative surgical device that is configured to rotate. An elongate member 104 of the rotatable surgical instrument 100 includes an outer tubular member 106, such as a sheath, which contains at least in part therein an inner tubular member (not shown, see FIG. 2) that is directly coupled to the distal tip 102. The elongate member 104 may be flexible or may be substantially rigid, depending on the uses for which the rotatable surgical instrument 100 is to be used.

In various examples, the outer tubular member 106 may be formed from stainless steel or any biocompatible material that is sufficiently resilient against the forces involved to safely contain various components disclosed herein. The outer tubular member 106 can be flexible, e.g., by including cuts in the outer tubular member 106 to enable to the outer tubular member 106 to be bent or otherwise flex before and during operation of the rotatable surgical instrument 100. The outer tubular member 106 can also vary in stiffness along its length. In the illustrated example, a bend 107 in the outer tubular member 106 and the elongate member 104 generally represents a deflection from a major axis 108 of the elongate member 104. In various examples, the elongate member 104 is configured to flex or bend to an angle of 45 degrees relative to a major axis 108 of the elongate member 104. However, the device in other embodiments could be bent up to 90 degrees. In such examples, certain components contained therein may also be flexible, as will be disclosed herein. In various examples, the distal tip 102 may also be stainless steel (e.g., 440 Stainless Steel) or any other biocompatible material that is sufficiently resilient to enable the distal tip 102 to cut, grind, or otherwise engage with the material to which the distal tip 102 is to be applied.

The rotatable surgical instrument 100 may include or may be attached to an adapter 110 and motor housing 112. The motor housing 112 is an attachment or adapter that is part of a handpiece where a motor (not depicted) resides. The motor causes the distal tip 102 to rotate at a desired rate while not inducing rotational force on the outer tubular member 106. In the illustrated example, the adapter 108 includes ports 114 for applying suction to facilitate removal of debris and/or irrigation of the distal tip 102 to facilitate operation of the rotatable surgical instrument 100, as disclosed in detail herein.

Figure 2:
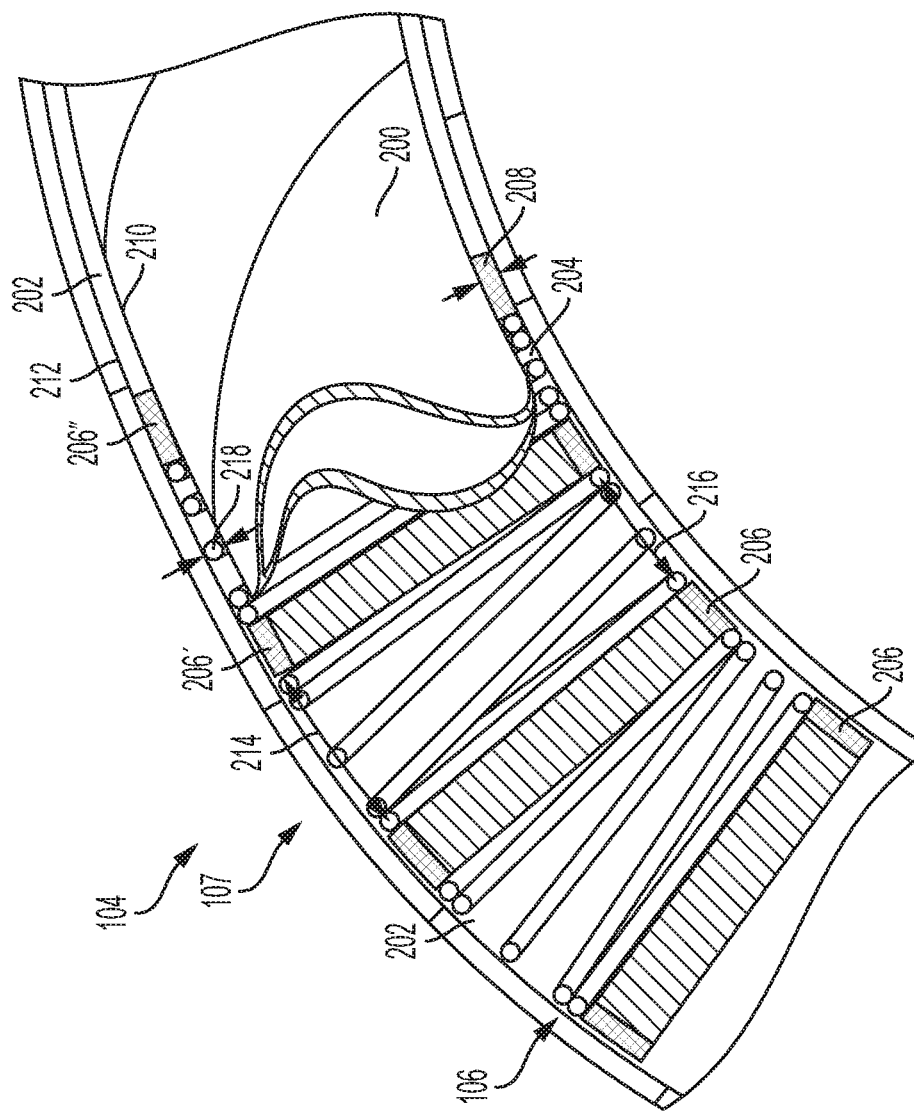
FIG. 2 is a cutaway detail image of the elongate member of the rotatable surgical instrument at the bend, in an example embodiment.

FIG. 2 is a cutaway detail image of the elongate member 104 of the rotatable surgical instrument 100 at the bend 107, in an example embodiment. The elongate member 104 further includes the inner tubular member 200 positioned within the outer tubular member 106. The inner tubular member 200 is coupled to the distal tip 102 and is coupled or coupleable to the motor. When the motor imparts rotational force on the inner tubular member 200 the inner tubular member 200 and the distal tip 102 may rotate together with respect to the outer tubular member 106. In various examples, the motor is configured to rotate the inner tubular member 200 and distal tip 102 at thousands or tens of thousands of revolutions per minute. In various examples, the inner tubular member 200 is made of metal formed into, e.g., a coiled flat wire or layers of flat wire comprising alternate wind directions, for example a clockwise outer layer and a counterclockwise wound inner coiled wire for example. or any suitable configuration to provide flexibility and transfer adequate rotational energy and torque to the distal tip 102.

For the purposes of clarity to illustrate other structures in the elongate member 104, only a portion of the inner tubular member 200 is illustrated. However, it is to be recognized and understood that in various examples the inner tubular member 200 extends from the distal tip 102 to the adapter 110 or, optionally, is operatively coupled to another member that is also seated in the outer tubular member 106 that ultimately couples to the adapter 110 and/or motor.

The inner tubular member 200 and outer tubular member 106 form a gap 202 therebetween, with spacers 204 and bearings 206 positioned in the gap 202. The bearings 206 have a thickness 208 sufficient to contact an outer surface 210 of the inner tubular member 200 and/or an inner surface 212 of the outer tubular member 106 in order to maintain a minimum separation between the inner tubular member 200 and the outer tubular member 106. The bearings 206 are positioned to prevent the outer surface 210 from contacting the inner surface 212. In the illustrated example, at least one spacer 204 is positioned between adjacent bearings 206, e.g., bearings 206', 206".

In the illustrated example, spacers 204 and bearings 206 alternate within the gap 202, with the spacers 204 positioned to prevent the bearings 206 from coming undesirably close to one another and possibly hindering the rotatable surgical instrument 100 from bending or imparting undesirable friction on the rotating inner member 200. In various examples, the spacers 204 maintain an approximate annular position of each of the bearings 206 along the elongate member 104. In various examples, lateral displacement of the bearings 206 along the elongate member 104 may maintain a minimum spacing between adjacent bearings 206 of at least approximately 1.016 millimeters (0.040 inches).

In the illustrated example, the spacers 204 are springs. The springs 204 provide a capacity both to provide counterforce against the bearings 206 to maintain the approximate lateral position of the bearings 206 along the inner tubular member 200 as well as flex and bend and thereby allow the elongate member 104 to flex. It is to be understood that many embodiments of the spacers 204 could be envisioned to provide spacing between the bearings 206. In an alternate embodiment (not shown), spring washers, wave washers, or the like may be employed. In further example embodiments, polymer spacers may be employed comprising a compressible foamed polymer (e.g., closed cell polyethylene), or conventional O-rings (e.g., silicone). As illustrated, a first apparent length 214 of a spacer 204 along a concave inner surface 212 is greater than the second apparent length 216 of the spacer 204 along the convex outer surface 210. In various examples, the spacers 204 have a thickness 218 less than the thickness 208 of the bearings 206 in order to promote the bearings 206 being contact with the inner surface 212 and outer surface 210. It is to be recognized and understood that the any mechanism that may maintain a relative lateral position of the bearings 206 along the inner tubular member 200 and still enable the elongate member 104 to flex may be utilized instead of or in addition to springs.

The bearings 206 may be configured to rotate with respect to the inner tubular member 200 and/or the outer tubular member 106 and vice versa. In various examples, the bearings 206 are bushings, roller bearings, ball bearings, or any suitable bearing. In various examples, the bearings 206 are bushings formed from any suitable, relatively low-friction material, such as ceramic, metals, or polymers. In various examples, the polymers may be ultrahigh molecular weight polyethylene, polyacetal, nylon, or polytetrafluoroethylene (PTFE).

While spacers 204 and bearings 206 are illustrated as alternating, it is to be recognized and understood that more than one spacer 204 may be positioned between adjacent bearings 206. Moreover, while spacers 204 are depicted as being positioned between all adjacent bearings 206, in certain circumstances all adjacent bearings 206 do not necessarily have a spacer 204 therebetween, but at least two adjacent bearings 206 do have a spacer 204 therebetween.

Moreover, while all of the spacers 204 are depicted as being the same and all of the bearings 206 are depicted as being the same, it is to be recognized and understood that different types of spacers 204 and bearings 206 may be utilized in different locations along the elongate member 104. For instance, in an example, a sequence of spring—bushing—roller bearing—bushing—spring may be implemented and repeated. Additional patterns and sequences may be implemented as desired for various uses of the rotatable medical instrument 100.

In various examples, the spacers 204 and bearings 206 are positioned in the gap 202 along a complete length of the elongate member 104 from the distal tip 102 to the adapter 110. Alternatively, the spacers 204 and bearings 206 may be positioned in the gap 202 in regions of the elongate member 104 that are configured to flex but not necessarily in regions of the elongate member 104 that are not configured to flex. In various examples, the elongate member 104 and/or the rotatable medical instrument 100 generally may incorporate one or more structures to contain spacers 204 or bearings 206 that are on the ends of the spacer 204 and bearing 206 sequences, e.g., proximate the distal tip 102 and proximate the adapter 110.

Figure 3:
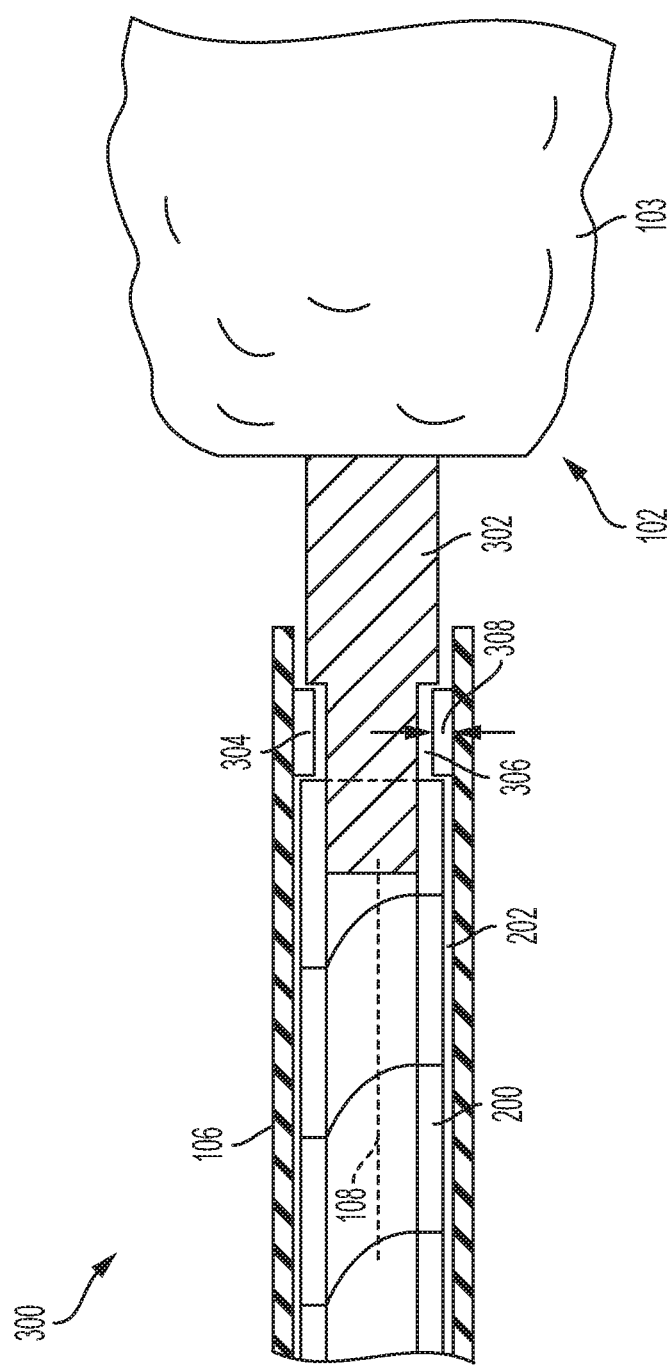
FIG. 3 is a detailed cutaway illustration of a junction between the distal tip and the inner tubular member, in an example embodiment.

FIG. 3 is a detailed cutaway illustration of a junction 300 between the distal tip 102 and the inner tubular member 200, in an example embodiment. The distal tip 102 includes the burr 103 and a shaft 302 that extends into the outer tubular member 106 and inner tubular member 200. A distal bearing 304 is positioned around the shaft 302 in a gap 306 between the shaft 302 and the outer tubular member 106. The gap 306 is in fluid communication with the gap 202 between the inner tubular member 200 and outer tubular member 106. For the purposes of simplicity, the spacers 204 and bearings 206 are not depicted, though it is to be recognized and understood that the such spacers 204 and bearings 206 may be extended down the elongate member 104 as depicted in FIG. 2. In the example of FIG. 3, the bearings 206 are proximal bearings 206 in contrast to the distal bearing 304. As such, in an example, a spacer 204 may be positioned next to and proximal to the distal bearing 304, followed by a proximal bearing 206, and so forth.

The shaft 302 is depicted as being secured to the inner tubular member 200 by being positioned within the inner tubular member 200. In various alternative examples, the shaft 302 may extend to but not be positioned within the inner tubular member 200. In such an example, the inner tubular member 200 may be secured, e.g., by welding or other suitable mechanism, to the end of the shaft 302.

In the illustrated example, the distal bearing 304 is a roller bearing that has a thickness 308 greater than the thickness 208 (FIG. 2) of the bearings 206. In various examples, the distal bearing 304 is the same as the bearings 206 and has the same thickness 208. The distal bearing 304 may inhibit a deflection of the distal tip 102 relative to the major axis 108 of the elongate member 104.

The positioning of distal bearing 304 generally maintains the distal tip 102 in a consistent position with respect to the outer tubular member 106 while the distal tip 102 is rotating. The distal tip 102 is generally inhibited from moving laterally along the major axis 108 of rotatable medical instrument as well as deflecting from or "wobbling" about the major axis 108. In an example, the distal tip 102 deflects from the major axis 108 by not more than approximately 2.54 millimeters (0.1 inches). As such, the rotatable medical instrument 100 may be relatively more stable and precise in use while also reducing wear and tear on the rotatable medical instrument 100 and on the motor and other ancillary equipment.

Figure 4:
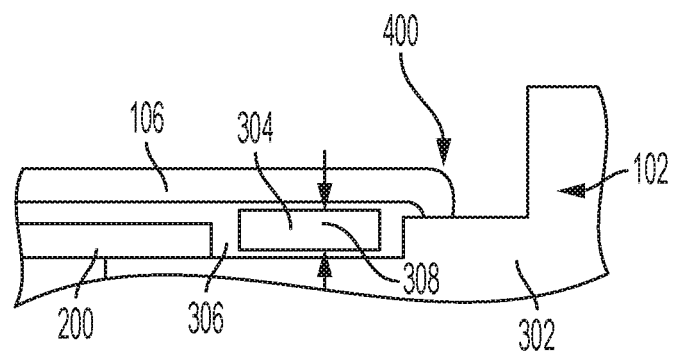
FIG. 4 is a detailed depiction of using a crimp to maintain an annular position of the distal bearing within the gap, in an example embodiment.

FIG. 4 is a detailed depiction of using a crimp 400 to maintain an annular position of the distal bearing 304 within the gap 306, in an example embodiment. In the illustrated example, the outer tubular member 106 has a crimp 400 proximate the shaft 302 of the distal tip 102. As illustrated, the crimp 400 places the outer tubular member 106 in contact with the shaft 302. However, in alterative examples, the crimp 400 may be such that the thickness 308 of the distal bearing 304 is greater than any resultant opening between the outer tubular member 106 at the crimp 400 and the shaft 302 so that the distal bearing 304 does not have a means of exiting the gap 306. The inner tubular member 200 bounds a proximal end of the gap 306.

Figure 5:
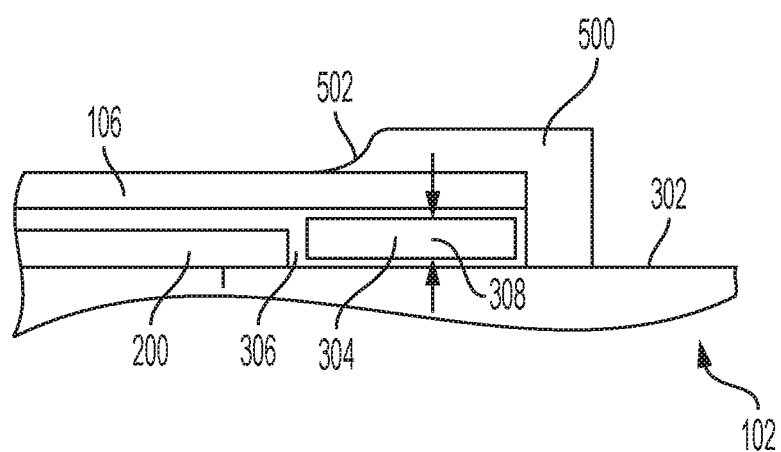
FIG. 5 is a detailed depiction of a retainer ring for maintaining an annular position of the distal bearing within the gap, in an example, embodiment.

FIG. 5 is a detailed depiction of a retainer ring 500 for maintaining an annular position of the distal bearing 304 within the gap 306, in an example, embodiment. The retainer ring 500 is secured to the outer tubular member 106, e.g., with a weld 502 or any other suitable fastener or fastening mechanism. The retainer ring 500 may be made from the same material as the outer tubular member 106. As with the crimp illustrated in FIG. 4, the retainer ring 500 may be positioned in contact with the shaft 302 or may leave an opening less than the thickness 308 of the bearing 304. The inner tubular member 200 bounds a proximal end of the gap 306.

Figure 6:
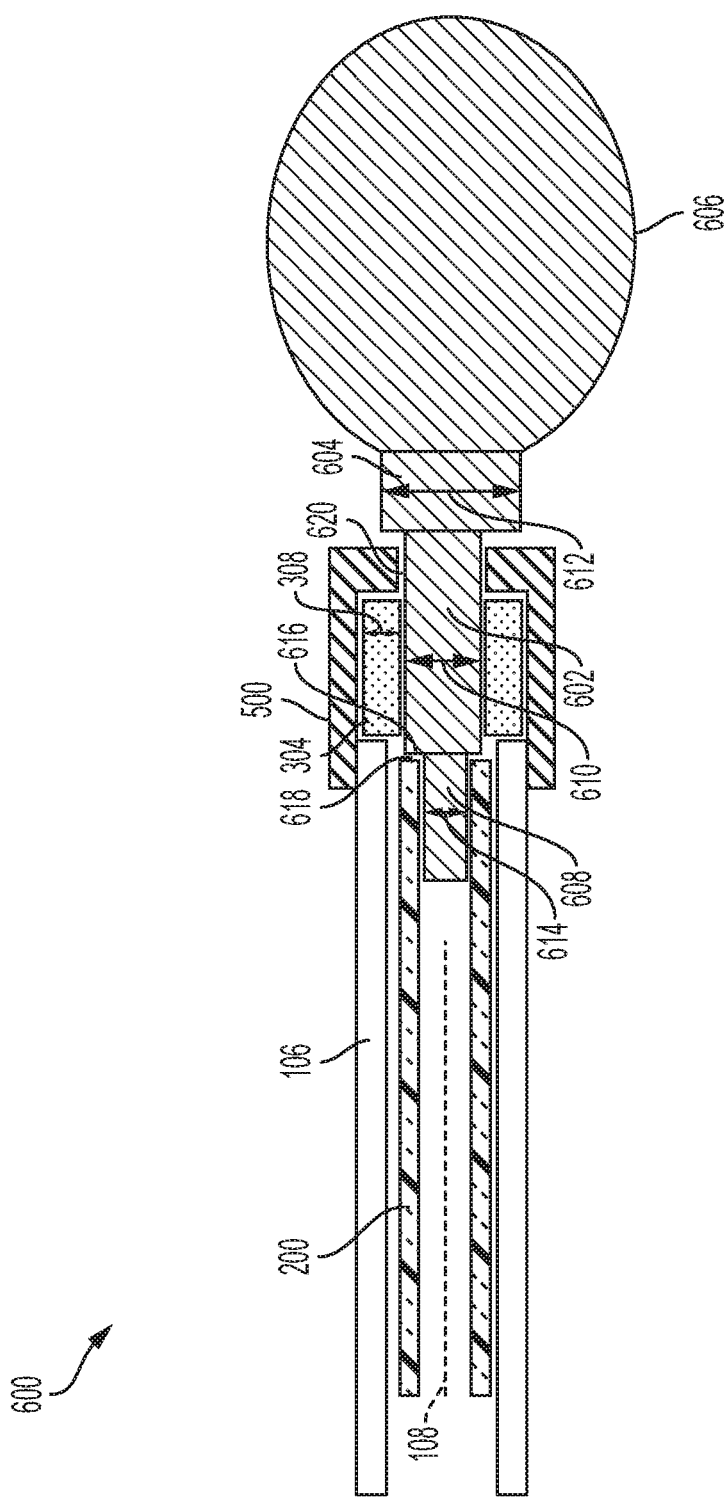
FIG. 6 is a detailed depiction of an alternative example of a distal tip used in conjunction with a retainer ring, in an example embodiment.

FIG. 6 is a detailed depiction of an alternative example of a distal tip 600 used in conjunction with the retainer ring 500, in an example embodiment. The configuration of the distal tip 600 may result in relatively less lateral movement of the distal tip 600 along the major axis 108. In particular, the distal tip 600 includes a primary stud 602 coupled to a base 604 of the burr 606 and a secondary stud 608 coupled to the primary stud 602. The primary stud 602 has a primary stud thickness 610 less than a base thickness 612 of the base 604 but greater than a secondary stud thickness 614 the secondary stud 608. While the distal tip 600 is described with studs, it is to be recognized and understood that any suitable structure may be utilized, such as hollow shafts and the like.

The secondary stud thickness 614 is less than an internal diameter of the inner tubular member 200, allowing the secondary stud 608 to be positioned in part within the inner tubular member 200. The primary stud thickness 610 is greater than the internal diameter of the inner tubular member 200 but less than the internal diameter of the outer tubular member 106 and the internal diameter of the bearing 304, allowing the primary stud 602 to be positioned in part in the outer tubular member 600 and bearing 304 but not within the inner tubular member 200. The base thickness 612 is greater than the internal diameter of any of the inner tubular member 200, the outer tubular member 106, and the bearing 304.

The retainer ring 500 is secured to the outer tubular member 106 according to any desired mechanism, including but not limited to a weld. As illustrated, a gap 620 is maintained between the retainer ring 500 and the stud 602, the gap 620 being less than the thickness 308 of the bearing 304. As a consequence of the relative dimensions of the distal tip 600, the inner tubular member 200, the outer tubular member 106, and the bearing 304, lateral movement of the distal tip 600 along the major axis 108 is inhibited. In particular, the contact of an edge 616 of the primary stud 602 with the end 618 of the inner tubular member 200 inhibits such lateral movement toward a distal end of the rotatable medical instrument 100.

Additional Notes

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The disclosure, therefore, is not to be taken in a limiting sense, and the scope of various embodiments includes the full range of equivalents to which the disclosed subject matter is entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense. Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products.

Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. An Abstract, if provided, is included to comply with United States rule 37 C.F.R. § 1.72(b), to allow the reader to quickly ascertain the nature of the technical disclosure. It is submitted with the understanding that it will not be used to interpret or limit the scope or meaning of the claims. Also, in the above Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A rotatable surgical instrument, comprising:
   an outer tubular member;
   an inner tubular member contained, at least in part, within the outer tubular member and configured to rotate relative to the outer tubular member, the inner tubular member and outer tubular member forming a gap therebetween;
   a distal tip coupled to and configured to rotate with the inner tubular member;
   bearings, each positioned in the gap and encircling the inner tubular member, wherein each bearing is configured to maintain a separation between the outer tubular member and the inner tubular member;
   a spacer positioned within the gap and between two of the bearings, wherein the spacer is configured to maintain a spacing between the bearings;
   wherein at least one of the bearings is a roller bearing;
   wherein the bearings include a distal bearing and a proximal bearing and wherein the distal bearing is the roller bearing; and
   a retainer ring, positioned around the outer tubular member and the distal bearing, configured to maintain an annular position of the distal bearing relative to the distal tip.

2. The rotatable surgical instrument of claim 1, wherein the retainer ring is welded to the outer tubular member.

3. The rotatable surgical instrument of claim 1, wherein the outer tubular member is crimped proximate the distal tip to maintain an annular position of the distal bearing relative to the distal tip.

4. The rotatable surgical instrument of claim 1, further comprising a plurality of spacers, wherein at least one spacer is positioned between adjacent bearings.

5. The rotatable surgical instrument of claim 1, wherein the spacer is a spring encircling the inner tubular member.

6. The rotatable surgical instrument of claim 1, wherein at least one of the bearings is a bushing.

7. The rotatable surgical instrument of claim 1, wherein the distal tip comprises a burr.

8. A rotatable surgical instrument, comprising:
an outer tubular member;
an inner tubular member contained, at least in part, within the outer tubular member and configured to rotate relative to the outer tubular member, the inner tubular member and outer tubular member forming a gap therebetween,
a distal tip coupled to and configured to rotate with the inner tubular member;
a distal bearing positioned in the gap and encircling the inner tubular member and wherein the distal bearing is a roller bearing; and
a retainer ring, positioned around the outer tubular member and the distal bearing, configured to maintain an annular position of the distal bearing relative to the distal tip.

9. The rotatable surgical instrument of claim 8, wherein the retainer ring is welded to the outer tubular member.

10. The rotatable surgical instrument of claim 8, wherein the outer tubular member is crimped proximate the distal tip to maintain an annular position of the distal bearing relative to the distal tip.

11. The rotatable surgical instrument of claim 8, further comprising
a plurality of bearings, each positioned in the gap and encircling the inner tubular member, wherein each bearing is configured to maintain a separation between the outer tubular member and the inner tubular member; and
a spacer positioned within the gap and between two of the bearings, wherein the spacer is configured to maintain a spacing between the bearings.

12. The rotatable surgical instrument of claim 11, further comprising a plurality of spacers, wherein at least one spacer is positioned between adjacent bearings.

13. The rotatable surgical instrument of claim 11, wherein the spacer is a spring encircling the inner tubular member.

14. The rotatable surgical instrument of claim 11, wherein at least one of the bearings is a bushing.

15. The rotatable surgical instrument of claim 8, wherein the distal tip comprises a burr.

16. A rotatable surgical instrument, comprising:
an outer tubular member;
an inner tubular member contained, at least in part, within the outer tubular member and configured to rotate relative to the outer tubular member, the inner tubular member and outer tubular member forming a gap therebetween,
a distal tip coupled to and configured to rotate with the inner tubular member;
at least three bearings, each positioned in the gap and encircling the inner tubular member, wherein each bearing is configured to maintain a separation between the outer tubular member and the inner tubular member;
a plurality of spacers positioned within the gap and encircling the inner tubular member, each of the plurality of spacers positioned between two of the bearings, each of the bearings separated by at least one of the plurality of spacers, wherein a spacer of the plurality of spacers is configured to maintain an annular position of at least some of the bearings along the inner tubular member;
wherein the plurality of spacers, the inner tubular member, and the outer tubular member are configured to allow the inner tubular member and the outer tubular member to flex.

17. The rotatable surgical instrument of claim 16, wherein, when the inner tubular member and the outer tubular member are flexed, at least one of the plurality of spacers has a first apparent length and a second apparent length greater than the first apparent length.

18. The rotatable surgical instrument of claim 17, wherein the plurality of spacers include at least two of: a spring, a compressible foam polymer, or an O-ring.

19. The rotatable surgical instrument of claim 16, wherein the bearings and the plurality of spacers alternate along a length of the inner tubular member.

20. The rotatable surgical instrument of claim 19, wherein each spacer is in contact with at least two adjacent bearings.

* * * * *

UNITED STATES PATENT AND TRADEMARK OFFICE
CERTIFICATE OF CORRECTION

Page 1 of 1

PATENT NO. : 11,638,589 B2
APPLICATION NO. : 17/026526
DATED : May 2, 2023
INVENTOR(S) : Sansoucy et al.

It is certified that error appears in the above-identified patent and that said Letters Patent is hereby corrected as shown below:

In the Claims

In Column 9, Line 23, In Claim 8, delete "therebetween," and insert --therebetween;-- therefor In Column 9, Line 40, In Claim 11, delete "comprising" and insert --comprising:-- therefor Signed and Sealed this
Sixth Day of May, 2025

Coke Morgan Stewart
*Acting Director of the United States Patent and Trademark Office*